(12) United States Patent
Sevrain et al.

(10) Patent No.: US 6,258,091 B1
(45) Date of Patent: Jul. 10, 2001

(54) BONE FASTENER AND INSTRUMENT FOR INSERTION THEREOF

(75) Inventors: Lionel C. Sevrain, Lake Oswego, OR (US); Christophe J-P Sevrain, Ridgefield, WA (US); Alan Shearin, Portland, OR (US)

(73) Assignee: Walter Lorenz Surgical Inc., Jacksonville, FL (US)

( * ) Notice: Subject to any disclaimer, the term of this patent is extended or adjusted under 35 U.S.C. 154(b) by 0 days.

(21) Appl. No.: 08/866,201

(22) Filed: May 30, 1997

Related U.S. Application Data

(63) Continuation-in-part of application No. 08/635,410, filed on Apr. 26, 1996, now Pat. No. 5,707,373.
(60) Provisional application No. 60/011,647, filed on Feb. 14, 1996, and provisional application No. 60/014,048, filed on Mar. 25, 1996.

(51) Int. Cl.$^7$ .................................................... A61B 17/56

(52) U.S. Cl. ................................ 606/72; 606/73; 606/71; 606/70; 606/69; 606/213; 606/215; 606/216; 606/232

(58) Field of Search .................................. 606/72, 73, 71, 606/70, 69, 213, 215, 216, 232; 411/259, 265, 266, 276, 122, 124, 338, 339, 392, 916, 917

(56) References Cited

U.S. PATENT DOCUMENTS

| | | |
|---|---|---|
| 276,135 | 4/1883 | Cooley . |
| 741,747 | 10/1903 | Walz . |
| 1,105,105 | 7/1914 | Sherman . |

(List continued on next page.)

FOREIGN PATENT DOCUMENTS

| | | |
|---|---|---|
| 1 089 116 | 9/1960 | (DE) . |
| 2 125 556 | 6/1972 | (DE) . |
| 28 06 609 B1 | 7/1979 | (DE) . |

(List continued on next page.)

OTHER PUBLICATIONS

Godman & Shurtleff, Inc., Neurosurgical Quality Instruments, 1965.*
Godman & Shurtleff, Inc., Burr Hole Buttons.*

(List continued on next page.)

*Primary Examiner*—Henry J. Recla
*Assistant Examiner*—(Jackie) Tan-Uyen T. Ho
(74) *Attorney, Agent, or Firm*—Harness, Dickey & Pierce, P.L.C.

(57) ABSTRACT

A bone member fastener for closing a craniotomy includes a cap and a base interconnected by a narrow cylindrical collar. The cap has an externally threaded stud that screws into an internally threaded bore of the collar, thereby allowing the cap and base to be brought into clamping engagement against the internal and external faces of a bone plate and surrounding bone. In a particularly disclosed embodiment, the base of the fastener is placed below a craniotomy hole with the collar projecting into the hole, and the stud of the cap is screwed into the bore of the base from above the hole to clamp a bone flap against the surrounding cranium. This device provides a method of quickly and securely replacing a bone cover into a craniotomy. The distance between the cap and base can be selected by how far the threaded stud of the cap is advanced into the internally threaded collar. The fastener is therefore adaptable for use in several regions of the skull having various thicknesses. An insertion tool with a long handle permits safe and convenient placement of the base between the brain and the internal face of the bone plate. Some disclosed embodiments of the fastener have a cap and base that conform to the curved surface of the skull, for example by having an arcuate shape or flexible members that conform to the curvature of the bone plate and surrounding cranial bone as the fastener is tightened.

36 Claims, 6 Drawing Sheets

U.S. PATENT DOCUMENTS

| | | | |
|---|---|---|---|
| 1,390,485 | | 9/1921 | Bell . |
| 1,510,416 | | 9/1924 | Pietz et al. . |
| 1,616,232 | * | 2/1927 | Roberts et al. .................... 411/338 |
| 2,077,804 | | 4/1937 | Morrison . |
| 2,238,238 | | 4/1941 | Westrope . |
| 2,329,471 | | 9/1943 | King . |
| 2,489,870 | | 11/1949 | Dzus . |
| 2,494,229 | | 1/1950 | Collison . |
| 2,511,051 | * | 6/1950 | Dzus ...................................... 606/73 |
| 2,576,649 | | 11/1951 | Slind . |
| 2,791,868 | | 5/1957 | Viken . |
| 2,846,744 | | 8/1958 | Becker . |
| 3,019,887 | * | 2/1962 | Lowden ............................... 198/711 |
| 3,281,171 | * | 10/1966 | Hughes ................................ 403/280 |
| 3,547,114 | | 12/1970 | Haboush . |
| 3,712,357 | | 1/1973 | Corbett et al. . |
| 3,741,205 | | 6/1973 | Markolf et al. . |
| 3,779,240 | | 12/1973 | Kondo . |
| 3,790,507 | | 2/1974 | Hodosh . |
| 3,875,936 | | 4/1975 | Volz . |
| 4,033,243 | * | 7/1977 | Kirrish et al. ......................... 411/38 |
| 4,116,200 | | 9/1978 | Braun et al. . |
| 4,219,015 | | 8/1980 | Steinemann . |
| 4,245,545 | * | 1/1981 | Freeman ............................... 411/342 |
| 4,275,490 | | 6/1981 | Bivins . |
| 4,360,025 | | 11/1982 | Edwards . |
| 4,503,848 | | 3/1985 | Caspar et al. . |
| 4,643,610 | | 2/1987 | Bien . |
| 4,651,724 | | 3/1987 | Berentey et al. . |
| 4,669,473 | | 6/1987 | Richards et al. . |
| 4,683,878 | | 8/1987 | Carter . |
| 4,688,561 | | 8/1987 | Reese . |
| 4,793,335 | | 12/1988 | Frey et al. . |
| 4,802,477 | | 2/1989 | Gabbay . |
| 4,875,815 | * | 10/1989 | Phillips, II ............................ 411/38 |
| 4,903,691 | | 2/1990 | Heinl . |
| 4,905,679 | | 3/1990 | Morgan . |
| 4,905,680 | | 3/1990 | Tunc . |
| 4,923,471 | | 5/1990 | Morgan . |
| 4,988,351 | | 1/1991 | Paulos et al. . |
| 5,013,316 | | 5/1991 | Goble et al. . |
| 5,087,202 | | 2/1992 | Krenkel . |
| 5,098,433 | | 3/1992 | Freedland . |
| 5,139,497 | | 8/1992 | Tilghman et al. . |
| 5,167,665 | | 12/1992 | McKinney . |
| 5,196,016 | | 3/1993 | Buser et al. . |
| 5,201,737 | | 4/1993 | Leibinger et al. . |
| 5,250,049 | | 10/1993 | Michael . |
| 5,268,001 | | 12/1993 | Nicholson et al. . |
| 5,269,784 | | 12/1993 | Mast . |
| 5,342,393 | | 8/1994 | Stack . |
| 5,346,492 | | 9/1994 | Morgan . |
| 5,350,399 | | 9/1994 | Erlebacher et al. . |
| 5,352,229 | | 10/1994 | Goble et al. . |
| 5,372,598 | | 12/1994 | Luhr et al. . |
| 5,433,053 | | 7/1995 | Tulloch . |
| 5,433,719 | | 7/1995 | Pennig . |
| 5,468,242 | | 11/1995 | Reisberg . |
| 5,501,685 | | 3/1996 | Spetzler . |
| 5,549,620 | * | 8/1996 | Bremer ................................. 606/151 |
| 5,578,036 | | 11/1996 | Stone et al. . |
| 5,601,558 | | 2/1997 | Torrie et al. . |
| 5,669,912 | | 9/1997 | Spetzler . |
| 5,707,373 | * | 1/1998 | Sevrain et al. ........................ 606/72 |
| 5,722,976 | * | 3/1998 | Brown ................................... 606/69 |
| 5,741,282 | * | 4/1998 | Anspach, III et al. .............. 606/151 |
| 5,800,436 | * | 9/1998 | Lerch .................................... 606/72 |
| 5,916,200 | | 1/1999 | Eppley et al. . |
| 5,928,244 | | 7/1999 | Tovey et al. . |
| 6,068,631 | | 5/2000 | Lerch . |

FOREIGN PATENT DOCUMENTS

| | | | |
|---|---|---|---|
| 296 14 920 U1 | | 10/1996 | (DE) . |
| 296 14 921 U1 | | 10/1996 | (DE) . |
| 296 14 922 U1 | | 10/1996 | (DE) . |
| 296 14 923 U1 | | 10/1996 | (DE) . |
| 29614920 | * | 11/1996 | (DE) ............................. A61B/17/88 |
| 0 290 138 A2 | | 4/1987 | (EP) . |
| 0 291 632 A1 | | 5/1987 | (EP) . |
| 0 433 852 A1 | | 6/1991 | (EP) . |
| 0 510 390 A1 | | 10/1992 | (EP) . |
| 2 386 301 | | 11/1978 | (FR) . |
| 2 631 539 A1 | | 5/1988 | (FR) . |
| H05-21954 | | 3/1993 | (JP) . |
| H05-220714 | | 8/1993 | (JP) . |
| 1512584 A1 | | 10/1989 | (SU) . |
| 1600713 | | 10/1990 | (SU) . |
| 1655477 A1 | | 6/1991 | (SU) . |
| PCT/US97/01398 | | 2/1997 | (WO) . |
| 97/29708 | | 8/1997 | (WO) . |

OTHER PUBLICATIONS

"Internal Fixation of Small Fractures," Technique Recommended by the AAO–ASIF Group, U. Heim & K.M. Pfeiffer, copyright Springer–Verlag, Berlin–Heidelberg, 1974, 1982 & 1988.

"Manual of Internal Fixation Technique," Recommended by the AO–Group, M.E. Mueller, M. Allgower & H. Willenegger, copyright Springer–Verlag, Berlin–Heidelberg, 1970.

Four pages from catalog of products offered by Codman & Shurtleff, undated, disclosing Burr Hole Buttons.

Translation of G 85 23 003.8 (Germany), Bone Plate, Feb. 1986, Oswald Leibinger Gmbh (Owner).

Hans G. Luhr, M.D., D.M.D., "Indications of Use of a Microsystem for Internal Fixation in Craniofacial Surgery," J. of Craniofacial Surgery, vol. 1, No. 1, Jan., 1990, pp. 35–52.

Howmedica International, Inc., "Vitallium—Verschiedene Implantate," p. 54.

Leibinger LP, "Leibinger," copyright 1995, (1 sheet).

Walter Lorenz Surgical, Inc., "Surgical Instrument Catalog 5th Edition," copyright 1993, pp. 10–11.

Walter Lorenz Surgical, Inc., 1.5/2.0mm Combination Titanium Osteosynthesis System, copyright 1994.

Aesculap CranioFIX brochure, dated Mar. 1998, (9 sheets), along with sixteen (16) sheets of color photographs of the corresponding instruments, set forth in the brochure.

Aesculap CranioFIX Titanium Clamp Instruction Manual (28 sheets) in various languages, dated Jan. 1999, along with one (1) color photograph of an Aesculap CranioFIX Titanium Clamp.

Codman & Shurtleff, Inc., Neurosurgical Quality Instruments, Copyright, 1965, pp. 10–13.

For The Few Who Know the Difference, TiMesh, Inc. (1 sheet).

Four pages from catalog of products offered by Codman & Shurtleef, undated, disclosing Burr Hole Buttons.

* cited by examiner

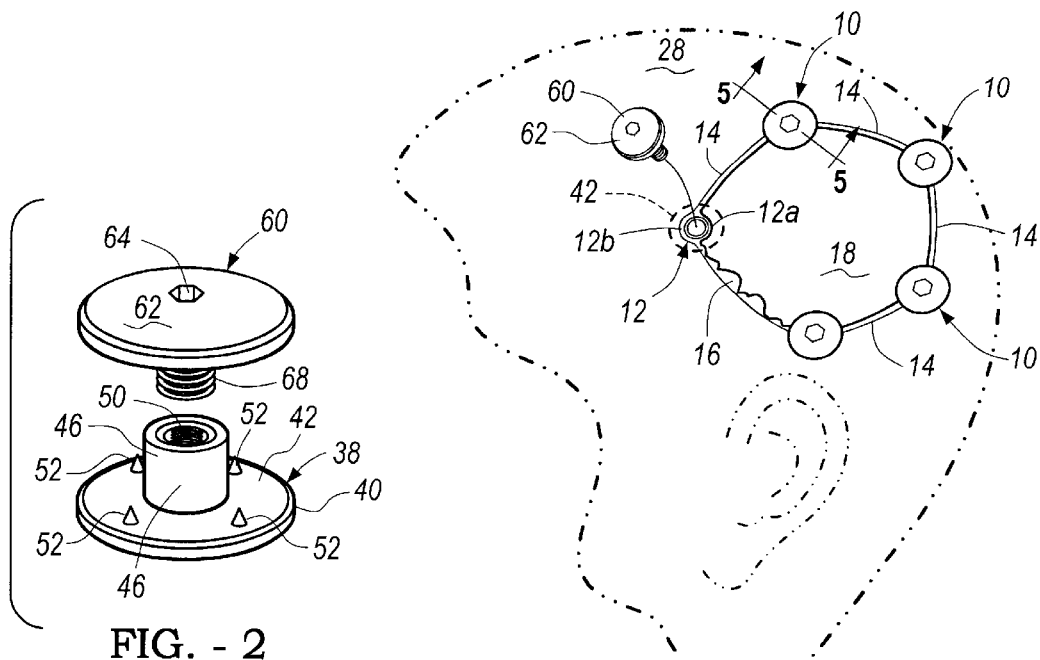
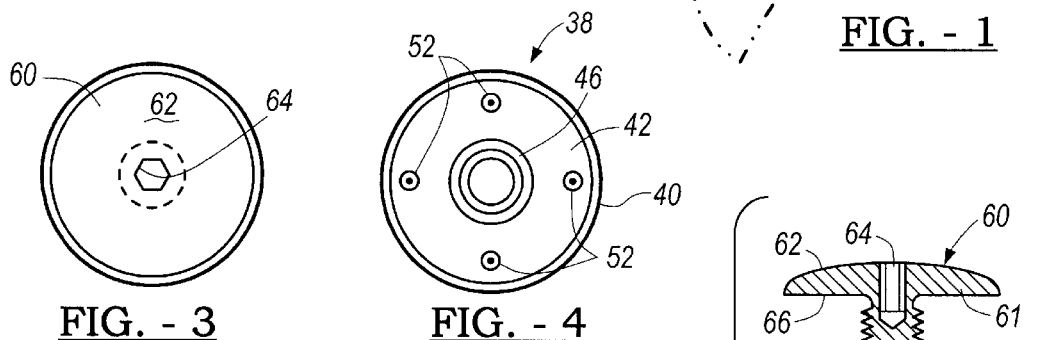
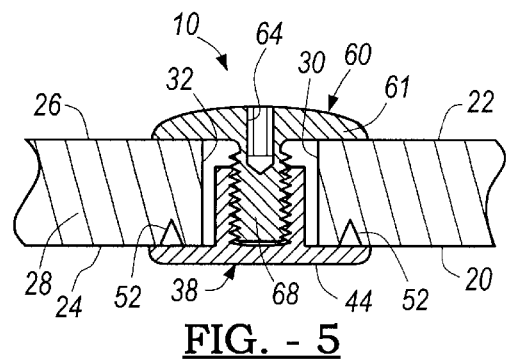
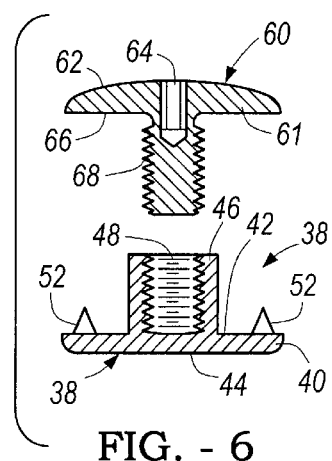
FIG. - 1
FIG. - 2
FIG. - 3
FIG. - 4
FIG. - 5
FIG. - 6

BONE FASTENER AND INSTRUMENT FOR INSERTION THEREOF

CROSS REFERENCE TO RELATED CASES

This case is a Continuation-In-Part of U.S. patent application Ser. No. 08/635,410 filed Apr. 26, 1996 U.S. Pat. No. 5,707,373, which claims priority from U.S. patent application No. 08/635,410 filed Apr. 26, 1996, which claims priority from U.S. Provisional patent application Ser. No. 60/011,647 filed Feb. 14, 1996, and U.S. Provisional patent application Ser. No. 60/014,048 filed on Mar. 25, 1996.

BACKGROUND OF THE INVENTION

1. Field of the Invention

This invention relates to a fastener for securing a bone plate to surrounding bone, for example when replacing a portion of the cranial vault removed during a craniotomy for a neurosurgical procedure. The invention also relates to an instrument for securing two threaded members to each other. The instrument may be used during neurosurgical procedures, or as a mechanical tool in many other contexts.

2. General Discussion of the Background

A craniotomy is a surgical procedure in which a portion of the cranial vault is removed or folded back in a flap to permit surgical access to the cranial contents (such as the brain). To perform the craniotomy, several burr holes are drilled through the skull. The number and position of these holes varies depending on the shape of bone to be removed. For example, three burr holes are drilled at corner points if a triangular bone flap is desired. The burr holes are then connected by osteotomy cuts, for example using a Gigli flexible saw which is passed internally between the burr holes. The saw is then oscillated back and forth to cut the skull along a line of separation (defined by the connecting osteotomies) connecting adjoining burr holes. The bone cover is subsequently lifted off the underlying dura mater to expose the brain. The bone cover may either be completely removed from the surgical site, or folded back in a flap along an uncut edge of the flap.

After completion of the operation, the bone cover must again be fixed in its original position to protect the underlying brain. Conventional craniotomy closure requires that holes be drilled in the bone plate and surrounding cranium along the osteotomy lines, and stainless steel wire or silk sutures are then passed through the holes to retain the plate in place. Unfortunately, drilling the holes is time consuming and potentially dangerous, because of the risk of introducing infection. The sutures are also unstable and prone to breakage. Suture instability or breakage can lead to dangerous movements of the cranial plate against the brain, with pathologic sequelae similar to a depressed skull fracture. The sutures closing the osteotomy lines are not aesthetically pleasing, because they can leave irregularities in the overlying surface of the face or scalp. This irregularity is particularly unsightly if the surface of the bone plate is not held substantially co-planar with the surrounding bone.

Various fixtures have previously been proposed for securing the bone cover to the surrounding cranium. U.S. Pat. No. 5,201,737 discloses a flexible plate having a plurality of vanes with holes for receiving bone screws. The plate is placed over a cranial burr hole and adjoining osteotomy lines to provide external fixation of the bone cover to the surrounding cranium.

Other external bone plates are shown in U.S. Pat. No. 4,651,724; U.S. Pat. No. 4,923,471; U.S. Pat. No. 5,139,497 and U.S. Pat. No. 5,372,498. All of these plates are designed for external application to fractured bones, and require placement of a plurality of screws through the plates. As with the plate in U.S. Pat. No. 5,201,737 discussed above, placement of multiple screws through the plates is time consuming, predisposes to catastrophic infection, and is difficult to remove once in place.

A variety of fixation devices are also known for fusing fractured bones. An example of such a device is U.S. Pat. No. 2,511,051, in which an externally threaded stud screws into an internally threaded shank. Movement of the stud into the shank is guided by an hexagonal wrench that is inserted through the shank into a countersunk receptacle on the tip of the threaded stud.

U.S. Pat. No. 3,875,936 shows an attachment for replacing a trochanteric head to the femur by providing a barbed shear washer between the femur and trochanteric head. U.S. Pat. No. 5,098,433 uses a winged compression bolt for fusing fractured bones. U.S. Pat. No. 5,196,016 and U.S. Pat. No. 5,433,719 discloses fixation pins or screws for retaining bone fragments against one another.

In spite of the use of a variety of fasteners in orthopedic and neurosurgical procedures, improved techniques are still being sought to secure a cranial cover to the surrounding cranium following a craniotomy. Improved methods and devices for securing the fasteners to the skull are also disclosed.

Accordingly, it is an object of the present invention to provide a fastener that is especially suitable for closure of craniotomies.

Yet another object is to provide such a fastener that can be quickly and efficiently installed, and which is capable of easy removal in the event that subsequent intracranial access is required for another neurosurgical procedure.

Yet another object of the invention is to provide such a fastener that avoids the aesthetic drawbacks of prior fasteners, such as large indentations in skin overlying the craniotomy.

It is another object of the invention to provide such a fastener, and an instrument for manipulating the fastener, that allows it to be easily inserted and removed, yet which provides a potentially permanent and reliable fixation of the cranial cover, thereby avoiding the potentially catastrophic neurological consequences that can result from dislodgement or depression of the cranial cover.

Finally, it is an object of the invention to provide an instrument that is useful for engaging first and second members to each other, particularly when the engagement must occur on opposite surfaces, and one of the surfaces is not easily accessible.

SUMMARY OF THE INVENTION

These and other objects are achieved by the bone cover fastener of the present invention, which has internal and external fastening members. At least one of the fastening members has a conforming surface that conforms to a curved surface, such as the inside surface of the cranial vault. In other embodiments, both the internal and external fastening members have conforming surfaces, such that a surface of the internal fastener conforms to the internal surface of the cranium, while the external fastener also has a surface that conforms to the external surface of the cranium.

In one embodiment, there is a connector on the internal fastening member and a connector on the external fastening member, and the connectors cooperatively hold the internal and external fastening members in a fixed relationship that fixes the bone cover in a defect from which the bone plate has been removed. The conforming surface may be a curved surface of the internal fastening member that seats against the inner face of the cranium. In particularly disclosed embodiments, the internal and external fastening members are curved plates that respectively conform to the internal and external curvature of the skull. Alternatively, the conforming surface may be provided by flexible struts that deform into a curved configuration as the fastener is tightened.

In other embodiments, a tab is provided on one of the fastening members to prevent relative rotation between the fastening member and the cranium. In particular, the tab is a relatively flat member that extends away from the internal fastening member a sufficient distance to be retained between the bone plate and the remaining cranium. The tab is sufficiently thin that it fits within the gap between the bone plate and surrounding cranium. When the external fastening member is rotated relative to the internal fastening members to interconnect threaded connectors, rotation of the internal fastening member is opposed by the tab which is retained within the gap formed by the cranial osteotomy incision.

One of the connectors may be an elongated, externally threaded stud that projects from the first fastening member, while the second connector may be an elongated internally threaded collar that projects from the second fastening member. The stud is rotationally threaded into the collar, with the collar extending between the fastening members. The collar fits through the burr hole of a craniotomy incision, and each fastening member is wider than the collar and the burr hole to provide clamping surfaces above and below the burr hole that engage the internal and external surfaces of the bone cover and surrounding cranium. Screwing the threaded stud into the internally threaded collar brings the opposing fastening members closer together, and tightens them against the internal and external surfaces of the bone cover and surrounding cranium. The fastening members overlap margins of the burr hole and adjoining osteotomy lines to securely fix the bone cover to the surrounding bone.

In a disclosed embodiment, one of the fastening members is a base which includes a disc having a flat inner face and a flat outer face. A plurality of raised barbs extend from the inner face of the base to provide frictional engagement between the disc and bone. The other fastening member is a cap with an outer face that may be flat or convex, and a recess is provided in the outer face for engaging a drive member that rotates the cap. An externally threaded stud projects from an inner face of the base and an internally threaded collar projects from an inner face of the cap. The stud is approximately as long as the collar. The stud may be screwed partially or entirely into the collar, depending on the thickness of the bone cover. Hence the fastener has the versatility to be used in different locations of the skull, where bone thickness varies.

The fastener is used in a method for fixing a bone plate, such as a cranial cover, in a bone defect, such as a craniotomy opening. The bone plate has opposing internal and external surfaces that are to be held in position substantially co-planar with internal and external surfaces of surrounding bone. The method provides the steps of placing the base and cap of the fastening member on opposing internal and external surfaces of the bone plate, with the collar projecting into the hole, and a portion of the base and a portion of the cap overlapping the border of the junction between the bone plate and surrounding bone. The base and cap are then rotated into threaded engagement with one another, until the cap and base tightly engage opposing surfaces of the bone plate and surrounding bone to clamp the bone plate in place. In particularly preferred embodiments, the fastener is placed through a craniotomy burr hole, with the cap and base covering and closing the burr hole.

In yet another embodiment of the invention, a fastening instrument is provided to secure first and second members to each other. The instrument includes a sleeve, a shaft or rod that slides within the sleeve, an attachment mechanism on the sleeve for engaging the first member to the instrument, and an engagement structure on the shaft that engages the second member and pulls it into engagement with the first member. In more particular embodiments, the sleeve includes a handle extending out from the sleeve, and the rod includes a handle that allows the rod to be rotated and reciprocated relative to the sleeve. There is a threaded tip on the rod that engages an internally threaded collar of the first member to screw the first and second member to be moved into engagement with each other.

In a more particular embodiment, the instrument includes a sleeve that has a handle (such as a rod or disc) extending from the sleeve. A rod slides within the sleeve, and has a threaded tip at a distal end of the rod, and a handle (such as a disc or curved hand grip) near a proximal end of the rod. The handle extends perpendicularly to the rod, and allows an operator to both rotate the rod and move the rod axially within the sleeve. A distal tip of the sleeve that surrounds the threaded rod has a plurality of locking members or prongs that extend from the tip of the sleeve and fit into complementary receptacles on one of the fasteners to lock the fastener to the tip of the sleeve, for example by frictional engagement of the prongs to one of the fasteners.

The instrument is designed to engage two threaded fasteners to each other. The fastener includes a cap and a base, and a receptacle in the cap that engages the prongs on the sleeve to lock the cap to the sleeve. The cap also includes an opening through which the rod can slide. The base of the fastener includes a post having both internal and external threads, and the threaded tip of the rod has threads that are complementary to the internal threads of the post. The cap has a collar with internal threads that are complementary to the external threads on the post.

The fasteners are attached to each other by first engaging the fastener cap to the sleeve of the base by introducing the prongs into the receptacles on the cap. The rod is then extended through the cap, and the base secured to the rod by threading the threaded tip of the rod into the internally threaded post of the base. The sleeve is then axially advanced over the rod until the external threads of the base post abut the internal threads of the cap collar. The rod and sleeve are then rotated relative to each other (for example by rotating the shaft) to screw the externally threaded tip of the post on the base into the internally threaded collar of the cap. The threaded rod tip is then unscrewed from the internally threaded post of the base. The connected fasteners may then be disengaged from the instrument, for example by pulling the instrument away from the fasteners to disengage the locking member from the fasteners. Alternatively, axial movement of the rod towards the fasteners brings the threaded rod tip into abutment against the internal threads of the post, and pushes the fasteners off the locking members to disengage the fasteners from the instrument.

The instrument of the present invention can be used with many different types of fasteners, in many situations where two fasteners must be secured to each other in a difficult to reach location. The instrument is particularly useful when the fasteners are to be secured to opposite faces of a barrier that inhibits access to both faces of the barrier. One particular fastener with which the instrument can be used is the bone cover fastener of the present invention.

BRIEF DESCRIPTION OF THE DRAWINGS

FIG. 1 is a schematic view of a portion of the human skull in which a craniotomy has been performed, and fasteners of the present invention have been placed to secure the cranial cover to surrounding cranium.

FIG. 2 is an enlarged, perspective view of one of the fasteners of the present invention, wherein the cap and base are disengaged.

FIG. 3 is a top view of the cap of the fastener of FIG. 2.

FIG. 4 is a top view of the base of the fastener of FIG. 2.

FIG. 5 is a cross-sectional view taken along section line 5—5 of FIG. 1.

FIG. 6 is a cross-sectional view of the fastener shown in FIG. 2.

DETAILED DESCRIPTION OF A PREFERRED EMBODIMENT

Figure 7:
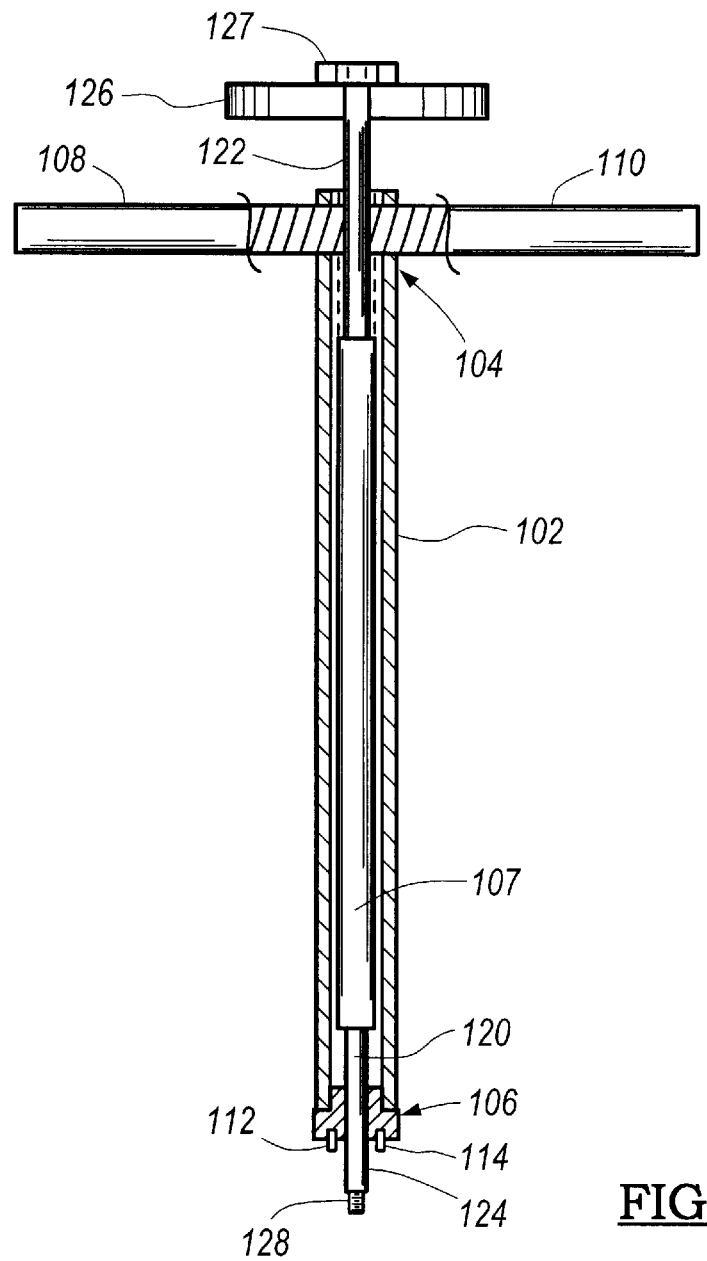
FIG. 7 is a cross-sectional view of a fastening instrument suitable for engaging another embodiment of the fasteners to one another.
Figure 8:
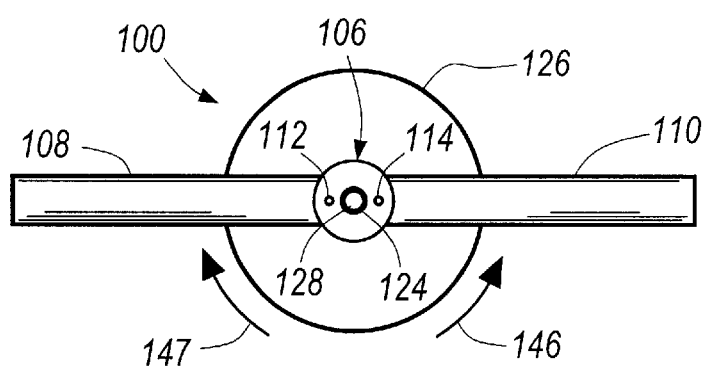
FIG. 8 is an end elevational view of the fastening instrument of FIG. 7.

The present invention includes fasteners for securing two table-like or curved plate structures to each other. The invention also includes a positioning instrument that is particularly useful for positioning the fasteners in a surgical wound, and a fastening instrument for securing the fasteners to each other. This detailed description will describe several embodiments of the fasteners, as well as an instrument that can engage the fasteners to each other. The instrument can be used to secure many different types of fasteners to each other, but is shown in connection with the neurosurgical fasteners for purposes of illustration.

A clamp 10 is shown in the drawings for closing a craniotomy (FIG. 1), which is a particular type of table-like structure. As is known in the art, a craniotomy is performed by incising pericranium and muscle with cutting diathermy in the line of an intended bone flap. An incision is not made interiorly where a pedicle of pericranium or temporalis muscle is often left uncut to allow some blood supply to the bone and overlying tissue to remain intact. Alternatively, the pericranium and muscle may be detached completely from the intended bone flap.

The craniotomy is performed by making a series of burr holes 12 through the cranium about six or seven centimeters apart with a conventional trephine. The underlying dura mater is separated from the bone covering the osteotomy site ("the bone cover") using a periosteal elevator. Osteotomies 14 between the burr holes 12 are then made using a Gigli flexible saw that is passed between adjacent burr holes and moved back and forth to make the osteotomies from the internal to the external surfaces of the cranium. The base of the flap, as illustrated in FIG. 1, is not made with a saw. A bone forceps (such as a de Vilbis forceps) is used to cut between burr holes until the bridge breaks at base 16 when the flap is elevated.

After placement of the burr holes and performance of the osteotomies, a bone plate 18 is separated from the surrounding cranium along a line of separation formed by osteotomies 14. Each burr hole 12 has a plate portion 12a and a complementary cranial portion 12b which together form the completed hole 12. Trephines come in graduated sizes, for example between 0.5 and 2 inches (13–51 mm) diameter, for drilling burr holes of sizes varying across this usual range.

The bone plate 18 may be completely removed if osteotomies connect all of the burr holes 12. However, it is often preferred to leave an intact edge of the craniotomy (such as 16) to preserve the blood supply to the bone (as shown in FIG. 1). In either case, the bone plate or flap is referred to as the cranial cover.

After the neurosurgical procedure is performed, the bone defect must be repaired by placing the cranial cover 18 back in the defect with opposing internal surface 20 and external surface 22 (FIG. 5) substantially co-planar or aligned with the internal surface 24 and external surface 26 of surrounding cranium 28 (FIG. 5). A transverse face 30 of bone cover 18 must also be fixed in apposition with a transverse face 32 of cranium 28, along a border of junction defined by the osteotomy 14 between bone cover 18 and surrounding cranial bone 28.

Structure of the Fastener

In one embodiment, the fastener 10 is a one-piece member that includes a base 38 (FIGS. 2, 4–6) formed by a solid disc 40 having a flat inner face 42 and a flat outer face 44. Inner face 42 circumscribes an elongated, cylindrical collar 46 projecting outwardly from the center of inner face 42. An internally threaded bore 48 extends longitudinally through collar 46, but does not extend through disc 40. Hence bore 48 in this embodiment communicates only with a round opening 50 at the top of collar 46, and does not extend through disc 40, which has a flat, solid, lower face 44. In other embodiments, bore 48 may extend through the base.

A plurality of raised, conical or pyramidal barbs 52 are integral with and extend upwardly from inner face 42 of disc 40. As best shown in FIG. 4, four barbs 52 are located on face 42, equally spaced around disc 40, and inwardly spaced from the perimeter of the disc. Barbs 52 taper to sharp tips 54 for engaging bone against which the barbs are placed, and into which the barbs may be embedded by pushing the barbs against the bone. The cancellous nature of the skull bone makes it particularly suitable for embedment of the barbs therein.

A cap 60 fastens to base 38 to form a fastener that secures bone cover 18 in place, and occludes the burr holes. Cap 60 is a solid disc 61 (FIGS. 5–6) with a convex outer face 62 that is smooth except for a recess 64 for engaging a complementary drive member (not shown) that rotates cap 60. The illustrated recess 64 is hexagonal, and designed to receive the tip of a surgical instrument resembling an Allen wrench. However, an elongated kerf could alternatively be scored in the surface 62 for receiving the tip of an instrument resembling a screw driver.

Cap 60 has a flat, annular inner face 66 from which an externally threaded stud 68 projects for inter-engagement with internally threaded bore 48 of collar 46. Stud 68 projects from the center of face 66, and the external threads are helical and machined to complement and screw into the internal helical threads of collar 46. Hence the collar resembles a nut into which the cap threads like a bolt. Stud 68 preferably has a length (extending perpendicularly away from face 66 along a longitudinal axis of fastener 10) that is approximately as long as threaded bore 48 of collar 46. The greatest width of cap 60 (as measured by the diameter of disc 61) and the greatest width of base 38 (as measured by the diameter of disc 40) are each wider than the outer diameter of cylindrical collar 46. The outer diameter of cylindrical collar 46 is less than the diameter of burr holes 12, but the diameters of discs 40 and 61 are greater than the diameter of burr holes 12. Cap 60 and base 38 each have a longitudinal axis of symmetry, such that the fastener when assembled is symmetric.

Method of Use to Close Craniotomy

The fastener 10 is used in a method of replacing a bone plate, such as cranial cover 18, following a craniotomy. As already described, the craniotomy is performed by providing a plurality of craniotomy holes, such as burr holes 12, through the skull. The burr holes are subsequently connected by osteotomies 14 to create a separation border for the cranial bone cover (which may be a plate that is removed or a flap that is folded back along one edge). The craniotomy opening therefore includes a portion 12a of burr hole 12 formed in cranial cover 18, and a complementary portion 12b of the hole formed in surrounding cranial bone 28.

Bone cover 18 has internal face 20 and external face 22 that are respectively placed in substantially co-planar relationship with internal face 24 and external face 26 of the surrounding cranial bone 28 when a craniotomy is closed. Opposing transverse faces 30, 32 of the bone cover and surrounding bone appose along the separation border when the bone cover is in place. Faces 30, 32 are substantially parallel to each other when in apposition.

In the method of the present invention, the bone cover 18 is folded back along a base 16, or completely removed as a plate, to expose the underlying dura mater and brain. Following the intracranial procedure, and prior to replacing the bone flap into its original orientation within the craniotomy opening, base 38 is placed below each burr hole 12 with the inner face 42 of base 38 against the internal surface 24 of cranium 28, such that one or more of barbs 52 engage the internal face 24. Base 38 overlaps the margins of hole 12 and the separation border between the cranial cover and surrounding bone (as shown in FIG. 1). Collar 46 projects upwardly into or through the portion 12b of the hole, but preferably does not extend out of the external surface. Cranial cover 18 is then replaced into the craniotomy opening, for example, by folding the bone flap along base 16 back down into the craniotomy opening.

Once cranial cover 18 is restored to its original position in the craniotomy opening, complementary portions 12a, 12b now reform hole 12. Collar 46 is centered in hole 12, with barbs 52 engaging the internal faces 20 and 24 of cover 18 and cranium 28 (FIG. 5). Cap 60 is then positioned over the reformed hole 12, with externally threaded stud 68 above opening 50. Stud 68 is introduced into collar 46 through opening 50, and a drive member (such as a surgical instrument resembling an Allen wrench) is inserted into hexagonal recess 64 to rotate cap 60 and advance stud 68 into threaded bore 48. Continued rotation of cap 60 diminishes the distance between base 38 and cap 60, to tighten inner faces 42, 66 of the base and cap against the internal and external surfaces of the cranium and cranial cover. The cap and base are thereby brought together in frictional engagement against opposing faces of the cranial cover 18 and surrounding bone 28, thereby clamping the cranial cover and surrounding bone to each other. Barbs 52 of base 38 anchor the base to both the cranial cover and surrounding bone, preventing rotation of the base while the cap is screwed into the collar. The base is attached to the bone as barbs 52 become progressively advanced into the bone by tightening of the fastener.

The fastener is used to clamp the cranial cover to the surrounding bone at one or more of the burr holes, and preferably all of the burr holes as shown in FIG. 1. A base 38 is therefore positioned below each burr hole 12 with collar 46 projecting up into the hole prior to replacement of cranial cover 18. A cap 60 is then screwed into each internally threaded collar until the cap and base clamp the bone cover 18 and surrounding cranium securely to each other. The cap and base are in a fixed relationship determined by the degree of advancement of the externally threaded stud 68 into the internally threaded collar 46, so that movement of the bone plate is substantially prevented. The bone plate and surrounding bone are held firmly in place with respect to each other, which avoids inadvertent depression of the cranial cover (with attendant catastrophic neurological consequences).

The smooth, convex top outer face 62 of cap 60 diminishes the aesthetic problem of visible indentations on the skull or face overlying the craniotomy burr holes. The closed base 44 tightly engages the internal surfaces of the cranial cover and surrounding cranium, providing ideal occlusion of the hole, to help avoid infection or trauma. The fastener also clamps the cranial cover in place quickly, thereby diminishing the period of time the brain must be exposed, and also reduces medical expenses associated with prolonged time in the operating room. The fastener is also easily removed, for example, by inserting an instrument into recess 64 of cap 60 and rotating the cap off of the fastener, to allow the bone flap to be subsequently removed if a follow-up neurosurgical procedure is required.

The fastener 10 is made of any biocompatible material, including stainless steel, titanium alloy, polyglycolic acid, silicone rubber, teflon or nylon. Titanium is a particularly preferred material. The biocompatibility of these and other materials can be enhanced by functionalization of the surface of the fasteners. Plasma gas discharge and corona treatment with reactive groups introduced on polymeric surfaces have been described as ways to modify biomaterial surfaces. See Lee et al., Biomaterials 12:443, 1991 and Lee et al., J. Colloid Interface Sci. 151:563, 1992.

The fastener 10 may be made in many different sizes. For purposes of illustration, the diameter of the stud 68 can be 7 mm (the same diameter as cylindrical bore 48); the external diameter of collar 46 may be 8 mm; the diameter of disc 61 can be 20 mm; the diameter of disc 40 may be 20 mm. In one preferred embodiment, stud 68 is 6 mm long, which is the same length as collar 46 and its internal bore 48.

The fastener of the present invention is adjustable for use in repairing craniotomies through bone of varying thickness. The pterion (in the temporo-parietal region) for example, is quite thin and may require a fastener with a 3 mm stud and collar, with advancement of the cap and base toward each other until the stud 68 has been completely advanced into collar 46 and face 66 of disc 61 abuts against collar 46. The 3 mm stud and collar, however, would also allow the fastener to clamp bones up to 6 mm thick (if the stud is only initially advanced into the collar). The parietal or frontal bone, however, may be 10–20 mm thick. A fastener with a 6 mm long stud 68 (and a 6 mm long internally threaded collar) can clamp bones together varying in thickness from 6 mm to 12 mm. A longer stud and collar (for example the stud and collar each 12 mm long) could clamp together bones from about 12 mm thick (when the fastener is fully tightened) to 24 mm thick (when the cap and base are initially engaged but before more rotation of the cap into the base occurs).

Other variations of the disclosed fastener are possible. The internally helically threaded collar, for example, may depend from the cap while the externally helically threaded stud may project from the base. The cap and base may assume many shapes other than circular, and may for example be square or triangular. Bone plates other than in the skull may be secured to surrounding bone, for example a relatively flat top bone such as the trapezium, mandible, maxilla, or bones of the orbit. The convex face of cap 60 may also be flat, particularly in areas of the skull (such as the temporal bone) with relatively flat external surfaces.

The fastener may also be used to fix adjacent members together, even where the members are curved. However, the embodiment of the fastener shown in FIGS. 16–23 is preferred for curved surfaces, and will be subsequently described.

Fastening Instrument

An instrument 100 for securing fastener members to each other is shown in FIGS. 7–12 to include an elongated tubular sleeve 102 (see especially FIG. 7) having a proximal end 104 (nearer the surgeon or other user) and a distal end 106 (farther away from the surgeon or other user). Two tubular handle members 108, 110 extend diametrically away from each other, perpendicular to the axis of sleeve 102. Distal end 106 has two small posts 112, 114 (FIGS. 7 and 8) projecting 1–3 mm (for example 2–3 mm) away from the flat surface 116 of distal end 106. Posts 112, 114 are spaced approximately 180° from each other, and serve as prongs that fasten the fastener to the instrument.

An elongated rod 120 (FIG. 7) slides within sleeve 102. A tubular guide member 107 may be placed in the sleeve 102 to fill empty space and inhibit relative transverse movement between the sleeve 102 and rod 120 that freely slides axially in the sleeve. Rod 120 includes a proximal end 122 and a distal end 124. A disc 126 is fixed to the proximal end 122 of rod 120 by hex nut 127, and extends perpendicularly to the longitudinal axis of rod 120. Disc 126 provides a handle on the instrument that can be grasped by a user to reciprocate or rotate rod 120 within sleeve 102.

The distal end 124 of rod 120 has an externally threaded, cylindrical, reduced diameter externally threaded tip 128. In one embodiment, sleeve 102 is approximately 14 cm long, with the span of arms 108, 110 being approximately 9 cm. Rod 120 is longer than sleeve 102, with a total length of approximately 16 mm from tip 128 to disc 126. The disc 126 is a solid, cylindrical disc having a diameter of approximately 3½ cm. Dimensions of the instrument may vary.

Instrument 100 is used to engage a first and second fastener to each other. In this disclosed embodiment, the first fastener is a cap 130, which is in the shape of a disc. Two openings 132, 134 through the disk are complementary to the size and location of posts 112, 114 on sleeve 102. Hence openings 132, 134 provide receptacles into which posts 112, 114 can be inserted and snugly received to secure or lock cap 130 to instrument 100, for example by frictional engagement between the posts 112, 114 and the receptacles in the cap 130.

A central opening 136 is provided through the center of the cap, along the axis of rotation of cap 130. Central opening 136 has a diameter only slightly greater than the diameter of rod 120, such that the rod can slide through and be guided by the walls of central opening 136. An internally threaded collar 138 (having helical internal threads) projects downwardly from cap 130 around central opening 136, and the central opening 136 communicates with and can extend through the collar 138.

The second fastener member is a base 140 which has the shape of a plate or disc with a central stud 142 projecting upwardly therefrom. Stud 142 is provided with external helical threads 144 that are complementary with the helical internal threads of collar 138, such that collar 138 can be rotated to thread cap 130 onto base 140.

Three sharp projections 150, 152, 154 extend upwardly from the disc of base 140 to help lock the base against a bearing surface. These projections 150–154 are located at the periphery of base 140, and are equally spaced about 60° from one another (such that all of the projections are on one-half of the base, preferably all within 120° of each other). The projections are substantially triangular, and each has a sharp apex that is suitable for embedment in a bearing surface (such as the internal surface of the skull).

Figure 9:
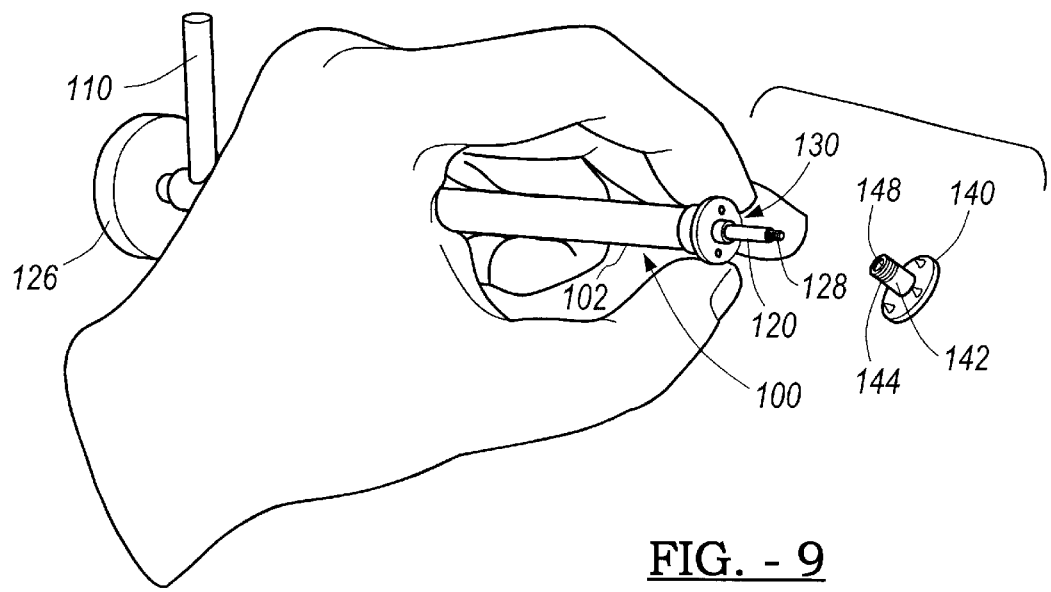
FIG. 9 is a view of a fastener instrument, showing the fastener cap secured to the instrument.

Use of the instrument 100 to rotate the cap and base relative to one another, for engaging them to each other, is demonstrated in FIGS. 9–12. FIG. 9 shows the first step, in which rod 120 is inserted through opening 136 of cap 130 until locking posts 112, 114 are inserted into openings 132, 134 and cap 130 is secured in place on end 106 of sleeve 102. The frictional engagement between locking posts 112, 114 and the receptacles formed by openings 132, 134 holds cap 130 on end 106.

Figure 10:
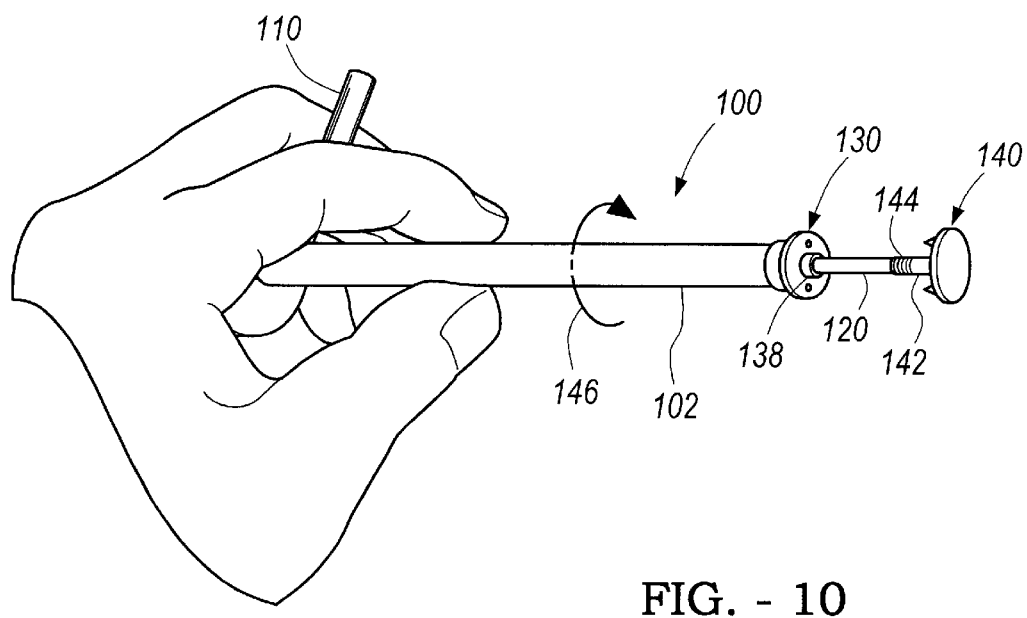
FIG. 10 is a view similar to FIG. 9, but showing both the fastener cap and base secured to the instrument.

As shown in FIG. 10, base 140 is then attached to rod 120 by inserting threaded tip 128 (FIG. 9) into internally threaded stud 142 of base 140 (while the base is secured in place against an inner face of the bone plate). Rod 120 is then rotated in the direction of arrow 146 (FIGS. 8 and 10) to screw threaded tip 128 into internally threaded stud 142 of the base. Rod 120 is rotated by turning disc 126 until base 140 is tightly secured on the tip. The step of threading base 140 onto tip 128 is preferably performed with rod 120 fully extended (as shown in FIG. 10) by exerting axial pressure against disc 126.

Figure 11:
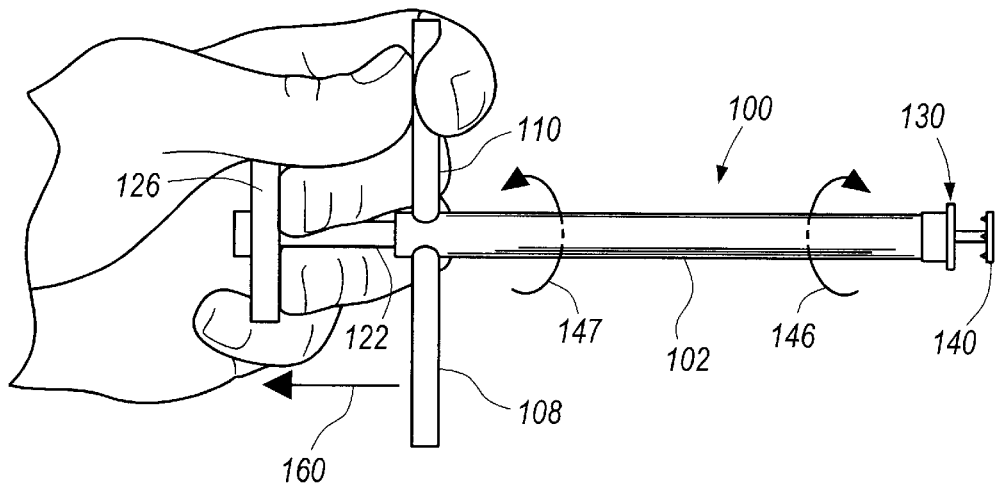
FIG. 11 is a view showing how the instrument is manipulated to rotate the fastener base relative to the fastener cap to secure the base and cap to each other.
Figure 12:
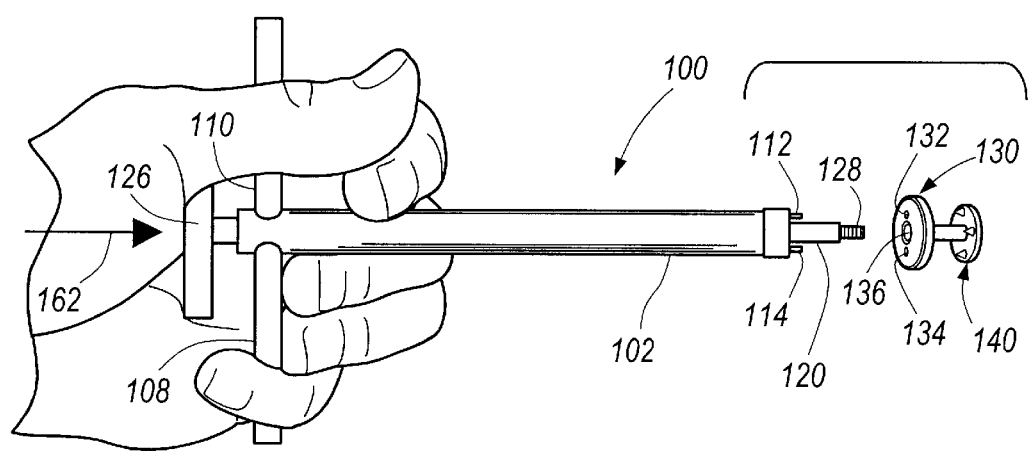
FIG. 12 is a view showing the instrument disengaged from the assembled fastener.

Rod 120 is then axially retracted relative to sleeve 102 (or sleeve 102 is advanced relative to rod 120) (FIG. 11) to introduce external helical threads 144 on the stud 142 into the internal helical threads in 138 of cap 130. With the rod in the fully retracted position, sleeve 102 is rotated by turning handle 110 in the rotational direction shown by arrow 146 (FIG. 11). Base 140 will remain stationary, because barbed projections 150–154 on the base engage bone, and inhibit rotation of the base. Hence rotation of sleeve 102 in the direction shown by arrow 146 screws internally threaded collar 138 on to externally threaded stud 142.

After collar 138 has been fully screwed on to base 140, disc handle 126 is then rotated in the direction of arrow 147 (the opposite direction of arrow 146) to unscrew threaded tip 128 of the shaft 120 from the internal threads of stud 142. When tip 128 is fully unscrewed from stud 142 and collar 138, the tip is axially retracted from opening 136 to fully disengage the instrument 100 from the fastener. When used in a surgical procedure, the instrument may then be withdrawn from the surgical wound, leaving the fastener firmly in place engaging the opposing faces of the bone plate and surrounding bone.

The fastening instrument 100 can also be used in non-surgical applications, for example securing a fastener to opposing faces of a work piece such as a wall or adjacent pieces of wood. Variations of the method of using the instrument can also be used, in both surgical and non-surgical applications. For example, the base 140 can be rotated to screw it on to threaded tip 128 instead of rotating threaded tip 128 to screw it into the base. Only relative rotation between the base and sleeve is needed. Similarly, the base collar can be screwed into the cap collar by providing relative rotation between the cap and base, without necessarily rotating the cap by turning the sleeve 102. The rod can instead be rotated (in a direction 147) to screw the base into the cap by relative rotation between the base and cap.

The relationships of the various parts of the instrument to the fastener are shown in the drawings, with particular reference to FIG. 11, wherein rod 120 has been axially retracted and cap 130 rotated relative to base 140 to attach the cap and base by threaded engagement of the helical threads. Base disc 140 has a lesser diameter than cap 130. In the disclosed embodiment, base disc 140 has a diameter of about 11 mm, while cap 130 has a diameter of about 13 mm. Stud 142 has a height of about 9 mm, while the height of collar 138 is about 4 mm. The smaller diameter of base disc 140 helps the base fit better against the interior face of the cranial vault, which has a steeper curvature than the curvature of the outer cranial cover.

The barbs 150, 152 and 154 are all within a 120° sector of base disc 140. This allows the barbs to be placed on the intact portion of the skull bone, without being embedded into the removable portion of the cranial cover. Hence the cranial cover can be removed when desired by disengaging the cap and base, without disengaging the barbs from the bone of the plate that is to be removed.

Alternative Embodiment of Fastener Instrument

Figure 13:
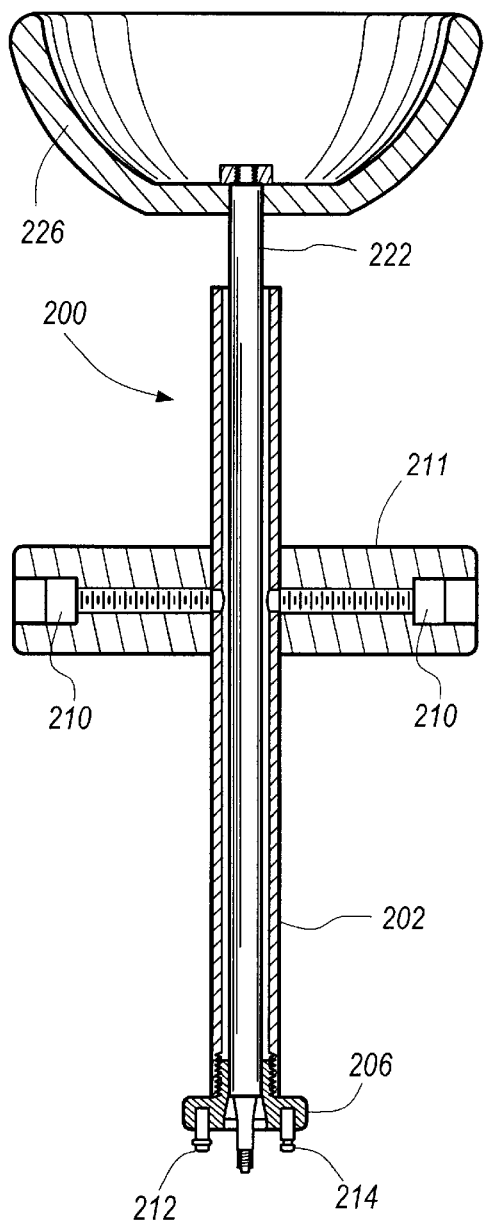
FIG. 13 is a side elevational view showing another embodiment of the fastening instrument, in which the sleeve handle is a disc and the rod handle is a curved handgrip.
Figure 13A:
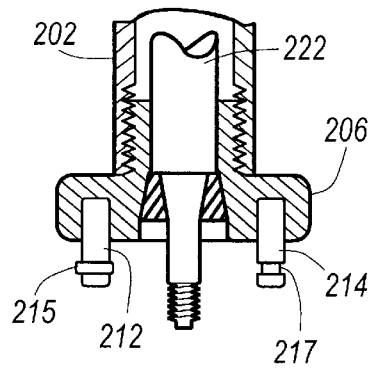
FIG. 13A is an enlarged view of the tip of the instrument shown in FIG. 13.

Another embodiment of the fastener instrument is shown in FIGS. 13–13A, and is designated instrument 200. This instrument is similar to instrument 100 shown in FIGS. 7–12, hence like parts have been given like reference numerals plus 100 to denote the similar parts, beginning with instrument 200. This embodiment differs, however, in that the rod handle 226 is not a disc, but is instead a handle grip with an arcuate frusto-hemispherical outer face. Alternatively, the handle 226 may be hemispherical or spherical in shape. The advantage of this shape is that it presents an arcuate side surface that can be easily grasped by the hand, with the fingers directed somewhat inwardly (toward the longitudinal axis of the instrument 200). Handle 226 provides a secure handgrip that is also easily rotated during use of the instrument.

The sleeve handle 210 also differs from the perpendicular rods 108, 110 that served as the sleeve handle in instrument 100. The sleeve handle is instead a disc that circumscribes the sleeve 202 and extends perpendicularly outwardly therefrom. The circumferential face 211 of disc 210 is serrated or otherwise roughened to increase frictional engagement between face 211 and the hand of a surgeon or other user of the instrument. Improved frictional engagement between the handle and hand is particularly helpful, for example, in surgical procedures during which blood or other body fluids may moisten the handle and make it slippery.

The friction engaging posts 212, 214 have also been elongated to 2–3 mm (for example 3 mm) to provide prongs that more securely hold the fastener cap on the instrument. The receptacle holes have been correspondingly elongated, and tightly engage the posts 212, 214 to selectively hold the instrument and fastener together. FIG. 13A also shows an alternative embodiment of the posts or prongs in which a circular coil spring or O-ring 215 (shown in place on post 212) is seated in an annular indentation (shown as 217) on each post. The coil spring is somewhat resilient, such that the spring is slightly compressed as posts 212, 214 are introduced into the receptacles of the cap. These compression springs provide improved engagement of the posts to the cap, such that the cap is even less likely to be dislodged from the instrument during use. Secure engagement of the cap to the instrument is important to allow the instrument to be manipulated, if desired, with one hand.

Figure 14:
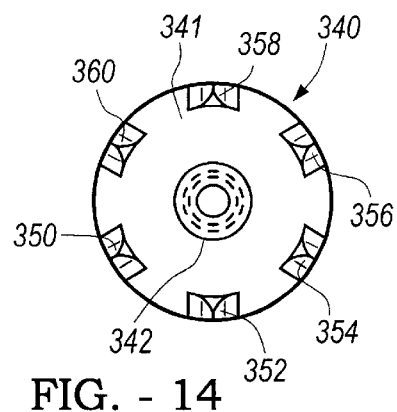
FIG. 14 is a top plan view of another embodiment of the base, showing distribution of the barbs around the inner face of the base.
Figure 15:
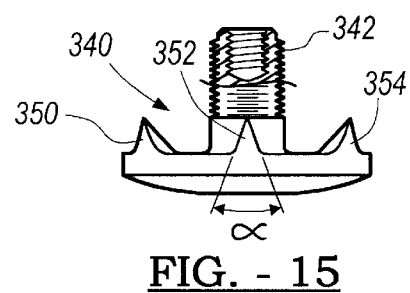
FIG. 15 is a side elevational view of the base shown in FIG. 14, illustrating the profile of the barbs.

Another embodiment of the fastener base is shown in FIGS. 14 and 15. The base 340 is shown with six barbs 350, 352, 354, 356, 358 and 360 distributed equally around the periphery of and extending from the inner face 341 of base 340. The barbs have a sharp profile, for example the apex of the barb forms and angle a that is about 30 degrees or less (FIG. 15). Each barb extends 2–3 mm in height above the surface of inner face 341. This height has been found to allow the barbs to enter bone (such as a bone plate) to a depth that provides particularly superior engagement between the fastener base and bone plate. Distribution of the barbs around the base (instead of placing the barbs in only a sector of the base, for example a 60° or 120° sector) allows the barbs to engage the bone plate even if the base rotates slightly from its original position of placement.

Alternative Fastener Embodiments

Figure 16:
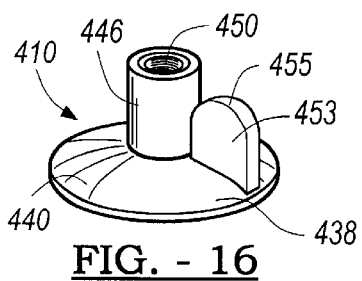
FIG. 16 is a perspective view of the base of another embodiment of the fastener, in which an inner face of the base is convex and an outer face (not shown) of the base is concave.
Figure 17:
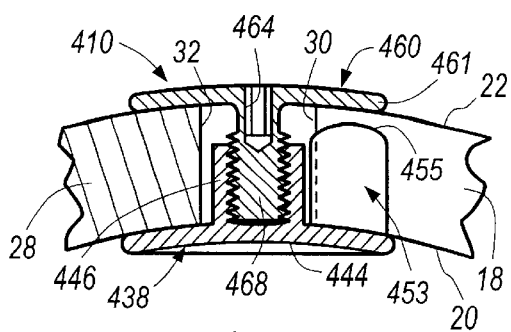
FIG. 17 is a cross-sectional view of the assembled fastener extending through a craniotomy burr hole and retaining a bone plate in place within a cranial defect.

Other embodiments of the fastener are contemplated as part of the present invention, and shown in FIGS. 16–23. A specific embodiment of the fastener 410, for example, is shown in FIGS. 16 and 17. That embodiment is similar to the fastener embodiment of FIGS. 5 and 6, except that the cap and base are curved to conform to the shape of the external and internal surface of the cranial vault. The range of curvatures of the human skull may range, for example, from a radius of curvature of 65–105 mm, and the radius of curvature of the cap and base can extend across this same range.

Fastener 410 includes a base 438 and a cap 460 made of polyethylene, and each having a surface with a radius of curvature of 84 mm that fits against the skull. The base (which is illustrated in isolation in FIG. 16) has a member 438 which is capable of conforming to the shape of a curved surface against which the member seats. In the disclosed embodiment of FIGS. 16–17, member 438 has a curved upper surface 440 which has a shape defined by a portion of a sphere. The curvature of surface 440 is substantially the same as a curvature of the internal surface of the bone plate 18 and surrounding bone 28 that form the internal face of the cranial vault. Bottom surface 444 of member 438 is also curved (and preferably parallel to curved surface 440) so that both the top and bottom surface of the base member 440 mimic the curve of the surrounding cranium. This curvature of the base helps member 438 fit against the internal face of the cranial vault, and avoids damage to surrounding dura mater that can occur when a flat plate fastener base does not conform well to the curvature of the skull.

In the disclosed embodiment, top member 461 of cap 460 is also curved to conform to the external curvature of the skull, such that cap 460 fits unobtrusively against the external surface of the skull. The curved cap is less obtrusive than a flate plate, and creates less of a post-surgical cosmetic defect in the overlying scalp. The curved plate creates less of a pucker in the overlying tissue.

Another feature of the fastener 410 is that it does not require barbs extending up from the base member 438 into bone to prevent relative rotation between base 410 and the bone against which the base seats. Instead, base 438 includes an upwardly extending tab 453 that extends into the osteotomy incision 14 between burr holes to oppose rotation of base 438 as cap 460 is screwed into it. Tab 453 is a projection that extends a sufficient distance from base 438 to be retained within the osteotomy incision. For example, the tab extends about at least one half the height of collar 446, or to a height the same height as the collar, or even slightly higher than the collar (as shown in FIG. 17). The range of tab heights, for example, may be 0.5 to 11.5 mm. Tab 453 is preferably a thin plate-like member that is substantially flat (with a thickness no greater than the osteotomy incision), for example, about 1–2 mm thick, or 1 mm thick, and extends radially from collar 446 substantially the entire radial width of base 438, and has a top that is not sufficiently sharp to penetrate bone). The illustrated tab 453 has a curved, blunt top 455.

Assembly of fastener 410 is illustrated in FIG. 17, which is similar to FIG. 5, and wherein like parts have been given like reference numerals plus 400, and the fastener 410 is positioned in a burr hole within an osteotomy separation. Base 438 can be positioned against the internal surface of bones 18, 28 such that the curved member 438 conforms to the shape of the skull, and tab 453 projects up into the osteotomy separation between bone plate 18 and surrounding bone 28. Base 438 can be placed in this position, for example, using the instrument shown in FIGS. 7–10 or FIGS. 13–13A.

Once the base 438 is appropriately positioned, cap 460 is then placed above the base, and externally threaded stud 468 is threaded into internally threaded collar 446 by rotating cap 460. Rotation of base 438 does not occur as cap 460 is rotated, because tab 453 is retained within the osteotomy incision and abuts against either the bone plate 18 or surrounding bone 28. Stud 468 is rotated into collar 446 until cap 460 and base 438 are appropriately tightened against the bone.

In an alternative embodiment of FIG. 16, the tab 453 can extend from collar 446 instead of surface 440. The base includes both surface 440 and collar 446.

Figure 18:
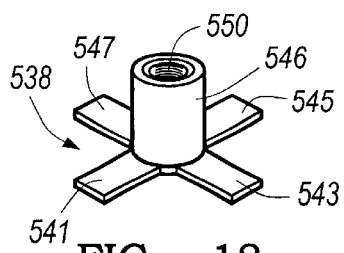
FIG. 18 is a perspective view of yet another embodiment of the base having flexible struts.
Figure 19:
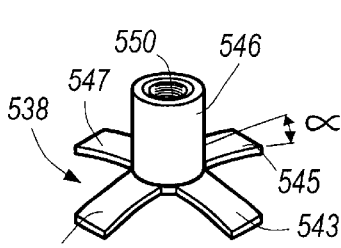
FIG. 19 is a view of the base shown in FIG. 18, but wherein the struts have flexed to conform to an interior curve of an internal face of a bone plate.
Figure 20:
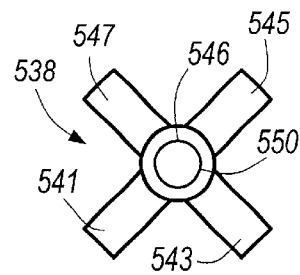
FIG. 20 is a top view of the base shown in FIG. 18.

Another embodiment of the fastener is shown in FIGS. 18–20, which show a strut embodiment of the base. The base 538 is made of four flexible strut members 541, 543, 545 and 547 that cooperatively form an "X" shaped base. Each strut is a thin, rectangular extension that is made of plastic (such as high density polyethylene) or other flexible material, and which can be flexed within about 2–15°, preferably at least 2°, of its resting position (as shown by a in FIG. 19) without breaking, and in the disclosed example flexes about 5°. Internally threaded collar 546 (having threaded bore 550 shown in FIG. 18) projects upwardly from the intersection of the struts, and is connected to a cap having an externally threaded stud (similar to the cap 460 shown in FIG. 17). As the cap is rotated relative to base 538, and base 538 tightens against the internal surface of bone plate 18 and surrounding bone 28, the flexible struts are bowed to conform to the curvature of the internal surface of the cranial vault.

Figure 21:
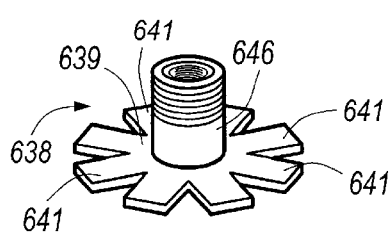
FIG. 21 is a view of another embodiment of the base which includes multiple struts.
Figure 22:
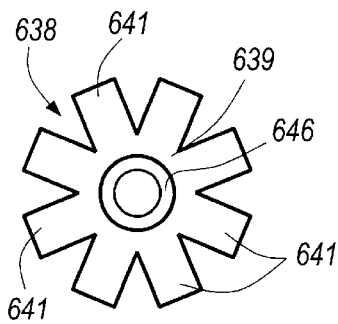
FIG. 22 is a top view of the base shown in FIG. 21.

Yet another embodiment of the strut base 638 is shown in FIGS. 21 and 22, wherein there are multiple thin flexible struts 641 extending from a central solid portion 639. Collar 646 projects upwardly from base 638. Collar 646 is externally threaded to accept an internally threaded cap, and is also internally threaded to accept the externally threaded tip of the insertion instrument. The thin struts 641 are approximately 1 mm thick, and may, for example, be 5–10 mm long.

Figure 23:
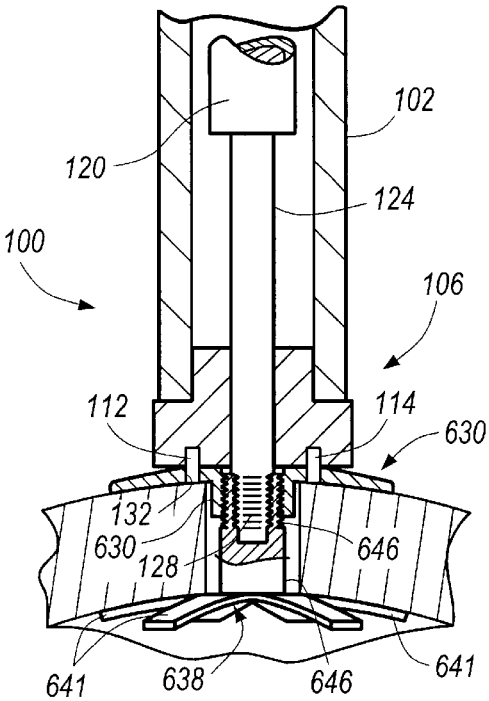
FIG. 23 is a cross-sectional view of the fastener shown in FIGS. 21 and 22, illustrating the fastening instrument that is used to assemble the fastener in the bone plate.

FIG. 23 shows the base of FIGS. 21 and 22 wherein the flexible struts 641 of the base are bowed to conform to the curvature of the internal skull as the curved cap 630 is tightened by screwing internally threaded cap 630 on to externally threaded collar 646. The fastening instrument 102 is also shown attached to the fastener, with threaded tip 128 screwed into the internal threads of collar 646 to hold base 638 against the internal surface of the cranium while curved cap 630 is rotated to screw internally threaded cap 630 on to externally threaded collar 646.

The flexible struts of the base provide more flexibility than a solid member. The struts are preferably made of a high density polyethylene. In the disclosed embodiment, each strut does not occupy more than about a 20–30° sector of the base. The disclosed struts are rectangular in shape, but they can alternatively taper, flare, or assume other shapes that sufficiently reduce the solid areas of the base to increase the flexibility of the base such that it conforms to the curvature of the skull when the fastener is tightened to such an extent that the bone in the skull is not fractured or damaged. For example, the modulus of flexibility of the base (or each individual strut) is 300,000 to 700,000 psi.

The fastener instrument of the present invention is preferably made of a metallic material that is suitable for sterile use in surgical procedures. Titanium or stainless steel are examples of such materials, particularly for the embodiments that do not flex. The fastener or instrument may also be made of a durable plastic material. Plastic is a particularly preferred material for embodiments of the invention that use flexible struts (such as the embodiments of FIGS. 18–23). The invention also includes a fastener, positioning instrument, and fastening instrument that has been sterilized, for example in an autoclave, or by irradiation (e.g. irradiation with ultraviolet radiation), or by chemical sterilization (e.g. with disinfectants or anti-microbials).

As used in this specification, the term "conforms to a curved member" does not require identical curvature of the conforming member and the surface to which it conforms. Substantial conformity of the members is all that is required, and that includes surfaces between flat planes and curves that precisely conforms to the curved member against which the conforming number slats.

Having illustrated and described the principles of the invention in several preferred embodiments, it should be apparent to those skilled in the art that the invention can be modified in arrangement and detail without departing from such principles.

We claim:

1. A method of holding internal and external surfaces of a cranial bone cover relative to internal and external surfaces of surrounding cranial bone, said method comprising:

performing an osteotomy to form the cranial bone cover having a first transverse face between the internal and external surface of the cranial bone cover and a second transverse face between the internal and external surface of the surrounding cranial bone;

providing a first fastening portion having a first inner face and a first outer face;

providing a second fastening portion having a second inner face and a second outer face;

providing an elongated member extending from the first fastening portion having a sidewall with a plurality of radially extending projections extending from at least a portion of the sidewall;

positioning the first inner face of the first fastening portion relative to the internal surfaces of the cranial bone cover and the surrounding cranial bone;

using a surgical instrument to adjustably position the second fastening portion relative to the first fastening portion by allowing the radially extending projections on the sidewall of the elongated member to engage the second fastening portion; and engaging the Internal and external surfaces of the cranial bone cover and the surrounding cranial bone with the first inner face of the first fastening portion and the second inner face of the second fastening portion to fix the first transverse face of the cranial bone cover in apposition with the second transverse face of the surrounding cranial bone and position the internal and external surfaces of the cranial bone cover substantially co-planar with the internal and external surfaces of the surrounding cranial bone.

2. The method as defined in claim 1 further comprising providing a plurality of barbs extending from the first fastening portion and engaging the plurality of barbs relative to the internal surfaces of the cranial bone cover and the surrounding cranial bone.

3. The method as defined in claim 1 further comprising providing a plurality of first fastening portions having different sizes and a plurality of second fastening portions having different sizes and selecting an appropriately sized first fastening portion and a second fastening portion.

4. The method as defined in claim 1 wherein the radially extending projections extend from at least a portion of an internal sidewall of a cylindrical collar and the second fastening portion is provided with a threaded stud extending from the second fastening portion.

5. The method as defined in claim 4 wherein the second fastening portion is adjustably positioned relative to the first fastening portion by threadably engaging the threaded stud with the cylindrical collar.

6. The method as defined in claim 1 wherein said first fastening portion and said second fastening portion are formed from a biocompatible material selected from a group consisting of stainless steel, titanium alloy, titanium, polyglycolic acid, silicon rubber, teflon and nylon.

7. The method as defined in claim 1 wherein only one of said first fastening portion and said second fastening portion includes a plurality of barbs extending from said fastening portion.

8. The method as defined in claim 1 wherein said first fastening portion is a first circular disk and said second fastening portion is a second circular disk.

9. The method as defined in claim 8 wherein said second outer face of said second fastening portion is a convex outer face.

10. The method as defined in claim 1 wherein said first fastening portion and said second fastening portion are formed from a biocompatible material selected from a group consisting of stainless steel, titanium alloy, titanium, polyglycolic acid, silicon rubber, teflon and nylon.

11. The method as defined in claim 1 wherein said surgical instrument adjustably positions said second fastening portion relative to said first fastening portion with said elongated member, whereby said elongated member prohibits axial displacement of said first fastening portion relative to said second fastening portion after said surgical instrument adjustably positions said second fastening portion relative to said first fastening portion.

12. The method as defined in claim 11 wherein said surgical instrument is operable to engage a recess formed in said second fastening portion.

13. The method as defined in claim 12 wherein said surgical instrument is selected from a group consisting of an Allen wrench and a screw driver.

14. The method as defined in claim 1 wherein said elongated member is integral with said first fastening portion.

15. The method as defined in claim 1 wherein said first fastening portion Includes a plurality of barbs having sharp tips operable to engage the cranial bone cover and the surrounding cranial bone to substantially prohibit rotation of said first fastening portion relative to the cranial bone cover and the surrounding cranial bone.

16. The method as defined in claim 15 wherein said plurality of barbs are circumferentially spaced about said first fastening portion.

17. The method as defined in claim 1 wherein said radially extending projections extend from at least a portion of an internal sidewall of a cylindrical collar.

18. The method as defined in claim 1 wherein said radially extending projections extend from at least a portion of an outer sidewall of a cylindrical stud.

19. The method as defined in claim 1 wherein said second fastening portion includes a second elongated member extending from said second fastening portion, said second elongated member operable to engage said elongated member extending from said first fastening portion.

20. A method of holding internal and external surfaces of a cranial bone cover relative to internal and external surfaces of surrounding cranial bone, said method comprising;

performing an osteotomy to form the cranial bone cover having a first transverse fare between the internal and external surface of the cranial bone cover and a second transverse face between the internal and external surface of the surrounding cranial bone;

providing a first fastening portion having a first inner face and a first outer face;

providing a second fastening portion having a second inner face and a second outer face;

providing an elongated member extending from the first fastening portion;

positioning the first inner face of the first fastening portion relative to the internal surfaces of the cranial bone cover and the surrounding cranial bone;

adjustably positioning the second fastening portion relative to the first fastening portion by engaging the elongated member with the second fastening portion; and engaging the internal and external surfaces of the cranial bone cover and the surrounding cranial bone with the first inner face of the first fastening portion and the second inner face of the second fastening portion and flexing the first fastening portion to conform to the internal surfaces of the cranial bone cover and the surrounding cranial bone as the first fastening portion is brought into engagement with the internal surfaces of the cranial bone cover and the surrounding cranial bone to fix the first transverse face of the cranial bone cover in apposition with the second transverse face of the surrounding cranial bone and position the internal and external surfaces of the cranial bone cover substantially co-planar with the internal and external surfaces of the surrounding cranial bone.

21. The method as defined in claim 20 wherein said elongated member includes a plurality of radially extending projections extending from at least a portion of a sidewall of said elongated member, said second fastening member operable to engage said radially extending projections.

22. The method as defined in claim 21 wherein said radially extending projections extend from at least a portion of an internal sidewall of a cylindrical collar.

23. The method as defined in claim 21 wherein said radially extending projections extend from at least a portion of an outer sidewall of a cylindrical stud.

24. The method as defined in claim 20 wherein said first fastening portion includes a plurality of barbs extending from said first fastening portion, said plurality of barbs operable to engage the cranial bone cover and the surrounding cranial bone.

25. The method as defined in claim 24 wherein said plurality of barbs taper to sharp tips and are integral with said first fastening portion.

26. The method as defined in claim 25 wherein said plurality of barbs are circumferentially spaced about said first fastening portion.

27. The method as defined in claim 20 wherein said elongated member includes a sidewall with radially extending projections extending from at least a portion of said sidewall, whereby said second fastening portion is operable to engage said radially extending projections on said sidewall of said elongated member to permit adjustable positioning of said first fastening portion relative to said second fastening portion.

28. The method as defined in claim 27 wherein said radially extending projections extend from at least a portion of an internal sidewall of a cylindrical collar.

29. The method as defined in claim 27 wherein said radially extending projections extend from at least a portion of an outer sidewall of a cylindrical stud.

30. The method as defined in claim 20 wherein said second fastening portion includes a second elongated member extending from said second fastening portion, said second elongated member operable to engage said elongated member extending from said first fastening portion.

31. The method as defined in claim 20 wherein only one of said first fastening portion and said second fastening portion includes a plurality of barbs extending from said fastening portion.

32. The method as defined in claim 20 wherein said first fastening portion and said second fastening portion are each formed as a circular disk with said second outer face of said second fastening portion having a convex outer face.

33. The method as defined in claim 20 wherein said first fastening portion and said second fastening portion are formed from a biocompatible material selected from a group consisting of stainless steel, titanium alloy, titanium, polyglycolic acid, silicon rubber, teflon and nylon.

34. The method as defined in claim 20 wherein said elongated member is integral with said first fastening portion.

35. The method as defined in claim 20 wherein said first fastening member and said second fastening member are formed from a biocompatible material selected from a group consisting of stainless steel, titanium alloy, titanium, polyglycolic acid, silicon rubber, teflon and nylon.

36. The method as defined in claim 20 wherein said first fastening member and said second fastening member are each formed as a circular disk with second outer face of said second fastening member having a convex outer face.

* * * * *

UNITED STATES PATENT AND TRADEMARK OFFICE
CERTIFICATE OF CORRECTION

PATENT NO. : 6,258,091 B1
DATED : July 10, 2001
INVENTOR(S) : Lionel C. Sevrain et al.

It is certified that error appears in the above-identified patent and that said Letters Patent is hereby corrected as shown below:

<u>Title page,</u>
Item [56] References Cited Foreign Patent Documents, delete "DE Reference No. 29614920" (Note: looks like # was corrected & new # is also listed on patent).

<u>Column 1,</u>
Line 7-8, delete "which claims priority from U.S.sSS. patent application 08/635,410 filed Apr. 26, 1996," (Note: duplicate info.).

<u>Column 9,</u>
Line 5, delete "teflon" and substitute -- Teflon -- therefor.

<u>Column 12,</u>
Line 51, "a" should be -- $\alpha$ --.

<u>Column 13,</u>
Line 30, delete "flate" and substitute -- flat -- therefore.
Line 52, "bone)" should be -- bone --.

<u>Column 14,</u>
Line 17, "a" should be -- $\alpha$ --.

<u>Column 15,</u>
Line 41, "Internal" should be -- internal --.

<u>Column 16,</u>
Line 7, delete "teflon" and substitute -- Teflon -- therefor.

Signed and Sealed this

Fourteenth Day of May, 2002

*Attest:*

JAMES E. ROGAN
*Attesting Officer*     *Director of the United States Patent and Trademark Office*

UNITED STATES PATENT AND TRADEMARK OFFICE
CERTIFICATE OF CORRECTION

PATENT NO.   : 6,258,091 B1
DATED        : July 10, 2001
INVENTOR(S)  : Lionel C. Sevrain et al.

It is certified that error appears in the above-identified patent and that said Letters Patent is hereby corrected as shown below:

Column 16,
Line 22, delete "teflon" and substitute -- Teflon® -- therefore.
Line 64, "fare" should be -- face -- therefore.

Column 18,
Lines 34 and 42, delete "teflon" and substitute -- Teflon® -- therefore.

Signed and Sealed this

Twenty-fifth Day of October, 2005

JON W. DUDAS
*Director of the United States Patent and Trademark Office*